(12) United States Patent
Harrison et al.

(10) Patent No.: US 8,786,860 B2
(45) Date of Patent: Jul. 22, 2014

(54) MEASUREMENT OF LIQUID FRACTION DROPOUT USING MICROPATTERNED SURFACES

(75) Inventors: Christopher Harrison, Auburndale, MA (US); Robert J. Schroeder, Cambridge, MA (US); Matthew T. Sullivan, Westwood, MA (US); Bradley Martin, St. Fargeau Ponthierry (FR); Albert Ballard Andrews, Wilton, CT (US); Oliver Clinton Mullins, Ridgefield, CT (US)

(73) Assignee: Schlumberger Technology Corporation, Sugar Land, TX (US)

( * ) Notice: Subject to any disclaimer, the term of this patent is extended or adjusted under 35 U.S.C. 154(b) by 322 days.

(21) Appl. No.: 13/277,933

(22) Filed: Oct. 20, 2011

(65) Prior Publication Data

US 2013/0100453 A1    Apr. 25, 2013

(51) Int. Cl.
*G01N 21/55* (2014.01)
*G01N 25/68* (2006.01)

(52) U.S. Cl.
CPC ..................................... *G01N 25/68* (2013.01)
USPC .......................................................... 356/445

(58) Field of Classification Search
USPC ................... 356/445; 374/18, 20, 28
See application file for complete search history.

(56) References Cited

U.S. PATENT DOCUMENTS

| 2,733,594 | A | * | 2/1956 | Silverman | 374/18 |
|---|---|---|---|---|---|
| 4,378,168 | A | * | 3/1983 | Kuisma et al. | 374/28 |
| 4,862,701 | A | * | 9/1989 | Small et al. | 62/150 |
| 4,946,288 | A | * | 8/1990 | Siska et al. | 374/20 |
| 5,299,867 | A | * | 4/1994 | Buck | 374/20 |
| 5,460,450 | A | * | 10/1995 | Buck | 374/20 |
| 6,170,267 | B1 | * | 1/2001 | Kitaoka | 62/3.6 |
| 6,575,621 | B1 | * | 6/2003 | Zlochin | 374/28 |
| 8,172,457 | B2 | * | 5/2012 | Boehm | 374/18 |
| 8,308,348 | B2 | * | 11/2012 | Boehm et al. | 374/28 |
| 2004/0042526 | A1 | * | 3/2004 | Zlochin | 374/16 |
| 2007/0147467 | A1 | * | 6/2007 | Arnold et al. | 374/28 |
| 2007/0171955 | A1 | * | 7/2007 | Kanai et al. | 374/28 |
| 2009/0296771 | A1 | * | 12/2009 | Boehm et al. | 374/19 |
| 2011/0188535 | A1 | * | 8/2011 | Boehm | 374/20 |

OTHER PUBLICATIONS

Dandekar, A.Y., Petroleum Reservoir Rock and Fluid, Taylor and Francis Group (2006) 8 pages.
Betancourt et al., "SPE 87011: Exploration Applications of Downhole Measurement of Crude Oil Composition and Fluorescence," SPE International, 2004: pp. 1-10.

* cited by examiner

*Primary Examiner* — Roy M Punnoose
(74) *Attorney, Agent, or Firm* — Jakub M. Michna; Bridget Laffey

(57) ABSTRACT

Accurate, real-time detection of dew point of a gaseous sample can be accomplished using the systems and techniques described herein. A gaseous sampling chamber defining an interior volume includes a patterned structure having a roughened surface exposed to the gaseous sampling chamber. The patterned structure includes an open volume accessible by the roughened surface, for example, representing at least about 10% of the interior volume of the gaseous sampling chamber. An illumination source is configured to illuminate at least a portion of the patterned structure. A light detector is configured to receive at least a portion of illumination returned from the patterned structure. A condensate detector is configured to determine a presence of a condensate on the roughened surface in response to an optical property of the patterned surface as modified by the presence of dew.

27 Claims, 12 Drawing Sheets

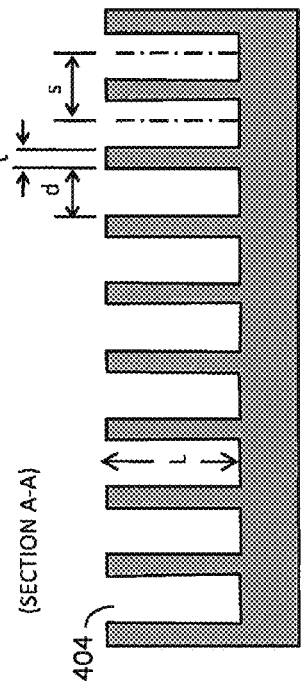
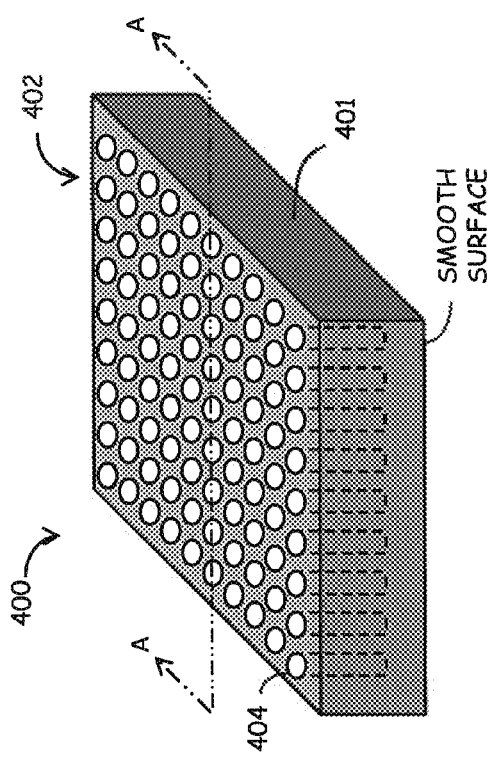
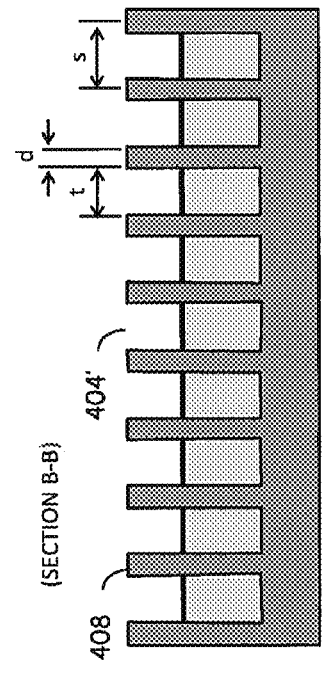
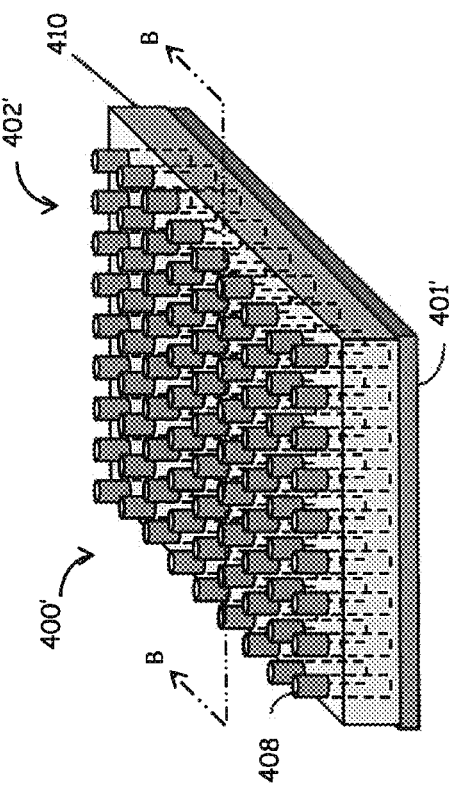

MEASUREMENT OF LIQUID FRACTION DROPOUT USING MICROPATTERNED SURFACES

BACKGROUND

1. Technical Field

This application relates generally to formation fluid analysis as may be accomplished downhole or at a surface. More particularly, this application relates to detection and identification of dew drop out in gaseous samples using patterned surfaces arranged to collect dew, the presence of dew determined by optical interrogation of the patterned surfaces.

2. Background Information

One of the fundamental challenges of measuring the dew point of a live gaseous sample is making an accurate measurement in the presence of filtrate contamination. The filtrate can be water or oil-based, adding a further complication that can be a source of contamination.

A measurement similar to a dew point determination is performed by the fluorescence detector in some formation evaluation tools. In such applications, however, pressure is not well-controlled. The fluorescence signal emerging from droplets condensing on a window abutting a flowline is used as an indication that the dew point has been reached. This signal, however, could potentially originate from fluorescence in the aqueous filtrate as well, producing an incorrect estimation of the dew point of the formation gas. An example is shown in FIG. 1, obtained by surface measurements with PVT Express, an onsite well fluid analysis service commercially available from Schlumberger Technology Corporation, Sugar Land, Tex., USA. PVT Express uses optical properties, such as refractive index, to detect two dew points (e.g., thought to be water and then alkane). The bottom trace originates from a sapphire probe that detects two dew points, one at 1300(s) and the other at about 2750 (s). The curve illustrates two dew points, leading to ambiguity that must be interpreted by the operator. The weakness of the signal should also be noted; the difference between single phase and dew is on the order of 0.03, for example, out of a magnitude of about 2.05, representing a change of only about 1% in signal magnitude.

SUMMARY

It would be desirable to differentiate between a dew consisting of filtrate-based contamination and one more representative of the formation gas itself. Furthermore, in either instance, it would be desirable to achieve a robust dew point and dew dropout fraction measurement that requires no direct human monitoring or monitoring of a sight glass.

Described herein are devices and techniques to attain one or more of dew point and liquid dropout measurements using patterned structures, e.g., with micro-faceted surfaces. In at least some embodiments, the patterned structures provide a tailored surface energy in a sensor as can be placed in a tool adapted for evaluation of subterranean formations. In at least some embodiments, such tailored surfaces can be fabricated to preferably condense either water or oil. By using such surfaces in conjunction with sensitive methods of optical detection and temperature control, it becomes possible to accurately determine a dew point of formation gases conveyed into an oilfield evaluation tool. Also described is a method to measure the volume fraction of dew dropout as a function of one or more of pressure and temperature.

In at least some embodiments, the volume fraction of dew dropout can be determined by an optical signal resulting from interrogation of the micro-faceted surfaces. For example, a greater reflectivity is obtained from a micro-faceted surface having a greater volume fraction of condensate. Conversely, less scattering is also obtained for a greater volume fraction of condensate. In at least some embodiments a relationship between an amount or range of volume fraction condensate for a particular micro-faceted surface can be predetermined, such that an estimate of the volume fraction can be obtained by a measurement of one or more of the reflectivity and scattering of the micro-faceted surface together with the predetermined relationship.

In one aspect, at least one embodiment described herein provides a condensate detector, including a gaseous sampling chamber defining an interior volume. The detector includes a patterned structure having a roughened surface that is at least partially exposed to the interior surface of the gaseous sampling chamber. The patterned structure includes an open volume that is accessible by the roughened surface. The open volume represents at least about 10% of the interior volume of the gaseous sampling chamber. The detector also includes an illumination source configured to illuminate at least a portion of the patterned structure. A light detector is configured to receive at least a portion of illumination returned from the patterned structure. The detector also includes a condensate detector in communication with at least the light detector. The condensate detector is configured to determine a presence of a condensate on the roughened surface in response to returned illumination received at the light detector.

In some embodiments, the light detector includes a detector array configured to selectively detect illumination returned from the patterned structure. The detector array, when provided, can be configured to detect illumination according to one or more of position and wavelength.

In some embodiments, condensate detector further includes an illumination source configured to optically excite fluids (i.e., condensate) on the patterned structure sufficiently to induce fluorescence in the condensate. In such embodiments, a light detector is configured to detect fluorescence spectra, such detection being indicative of a condensate.

In some embodiments, the condensate detector includes at least one window aligned between the roughened surface and each of the illumination source and the light detector. The at least one window isolates the illumination source and light detector from exposure to gaseous samples within the chamber, while allowing for efficient transmission of the illumination and the returned illumination therethrough. In some embodiments, the window includes the patterned structure.

A thermal source, such as a heater and/or cooler, can be provided in thermal communication with the patterned structure. The thermal source is operable to change a temperature of the roughened surface, for example, to selectively evaporate condensate from the roughened surface. Those skilled in the art can appreciate that miniaturization of the condensate surface structures, such as the micro-faceted and/or roughened surfaces described herein, accelerates making such measurements by reducing the amount of time necessary for cycling through temperatures (e.g., up and down for repeated measurements).

In some embodiments, the gaseous chamber is sealable and reconfigurable to at least one of increase and decrease the interior volume, inducing a corresponding change in pressure of a sample gas contained therein.

In some embodiments, the gaseous chamber further includes an outer layer disposed at least upon the roughened surface exposed to the gaseous sampling chamber, the outer layer operable to preferentially condense one of a water and a hydrocarbon.

In another aspect, at least one embodiment described herein provides a process for detecting a condensate in a gaseous sample. The process includes receiving the gaseous sample within a chamber defining an enclosed interior volume. A roughened surface of a patterned structure is exposed to the gaseous sample. The patterned structure includes an open volume that is accessible by the roughened surface. The open volume represents at least about 10% of the interior volume of the chamber. The patterned structure is illuminated and at least a portion of the illumination returned from the patterned structure is detected. A presence of the condensate on the roughened surface is determined from the detected illumination.

In some embodiments, illuminating the patterned structure includes optically exciting fluids on the patterned structure sufficiently to induce fluorescence in a condensate when present. The act of detecting the illumination includes detecting fluorescent spectra, such that the presence of condensate determinable from the detected fluorescent spectra.

In some embodiments, the process further includes determining from the detected illumination, a relative volume fraction dropout.

The act of detecting at least a portion of the illumination can include detecting reflected illumination, such that the presence of condensate on the roughened surface determinable from the reflected illumination. In some embodiments, the act of detecting at least a portion of the illumination includes detecting scattered illumination, such that the presence of condensate on the roughened surface determinable from the scattered illumination.

In some embodiments, the process further includes varying at least one of a temperature and a pressure of the gaseous sample, followed by repeating the acts of exposing, illuminating, detecting and determining a presence of the condensate. The act of varying at least one of a temperature and a pressure can include reducing a pressure, such that the pressure at which a presence of the condensate on the roughened surface is determined being indicative of a retrograde dew point.

In some embodiments, the process further includes selectively rejecting one of water and oil from the opened surface of the roughened surface, for example being treated with a coating that is hydrophobic or hydrophilic.

In yet another aspect, at least one embodiment described herein provides a condensate detector, including means for receiving the gaseous sample within a chamber defining an enclosed interior volume. The detector also includes means for exposing a roughened surface of a patterned structure to the gaseous sample. The patterned structure includes an open volume accessible by the roughened surface. The open volume represents at least about 10% of the interior volume of the chamber. Also provided are means for illuminating the patterned structure, means for detecting at least a portion of the illumination returned from the patterned structure, and means for determining from the detected illumination a presence of the condensate on the roughened surface.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 10A shows a perspective schematic diagram of an embodiment of a patterned structure.

FIG. 10B shows a cross-section of the patterned structure shown in FIG. 10A.

FIG. 11A shows a perspective schematic diagram of another embodiment of a patterned structure.

FIG. 11B shows a cross-section of the patterned structure shown in FIG. 11A.

DESCRIPTION OF THE PREFERRED EMBODIMENTS

Figure 1:
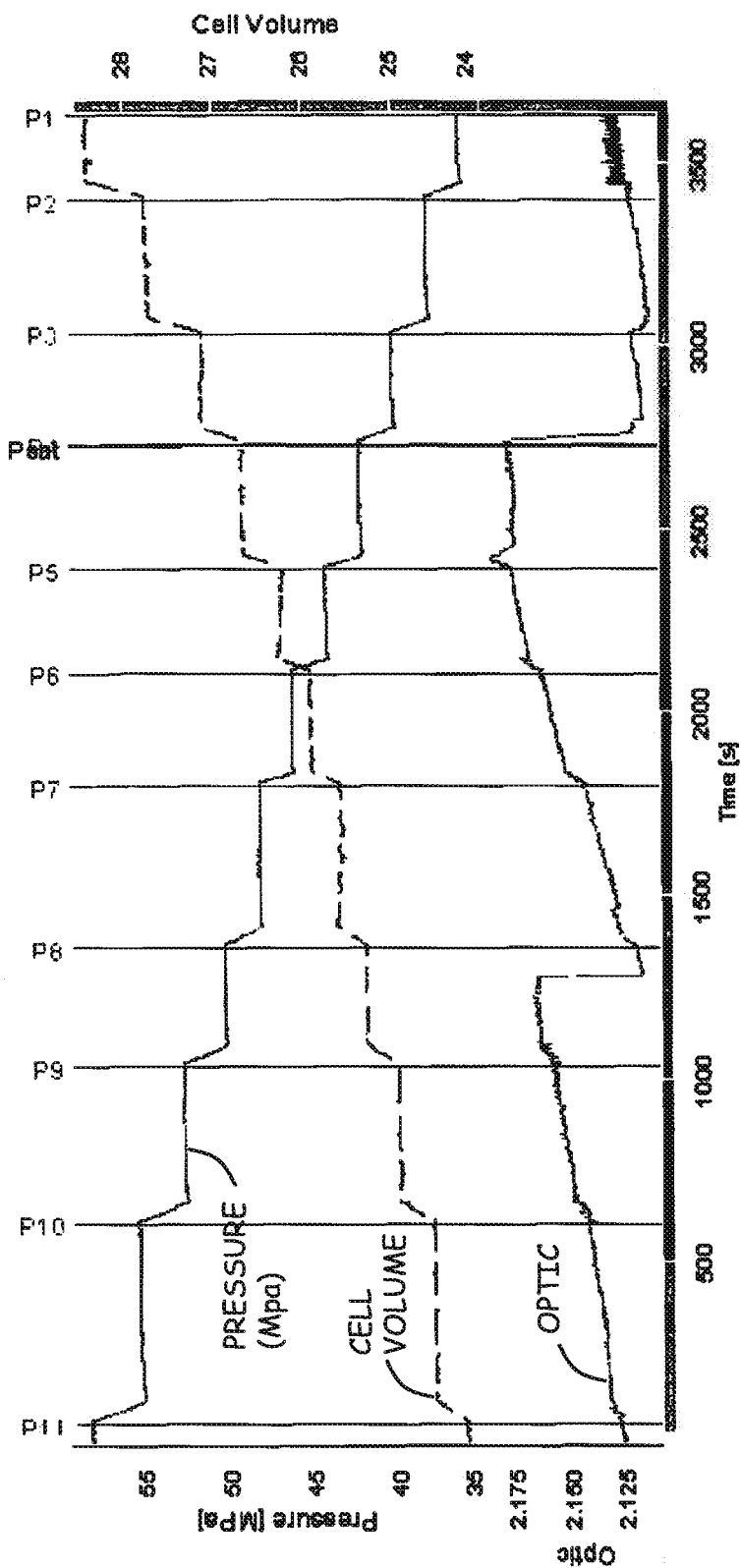
FIG. 1 shows dew point measurements obtained using a prior art device.

In the following detailed description of the preferred embodiments, reference is made to accompanying drawings, which form a part thereof, and within which are shown by way of illustration, specific embodiments, by which the invention may be practiced. It is to be understood that other embodiments may be utilized and structural changes may be made without departing from the scope of the invention.

The particulars shown herein are by way of example and for purposes of illustrative discussion of the embodiments of the present invention only and are presented in the case of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in that how the several forms of the present invention may be embodied in practice. Further, like reference numbers and designations in the various drawings indicate like elements.

Described herein are devices and techniques for measuring dew point of a fluid sample, such as a reservoir hydrocarbon in the gaseous phase. For a multi-component gaseous mixture in the single-phase, the dew point curve is defined as the locus of temperature and pressure points where liquid droplets begin to condense from the single phase gas. The dew point can be reached by reducing the temperature, or for a retrograde condensate, decreasing the pressure, or some combination of both temperature and pressure. It is likely that the latter dew point is more relevant for condensate wells in which the dew point pressure is especially valuable as it determines a maximum "drawdown" pressure allowed during production. At pressures below this point, flow through the reservoir will be impeded by liquid dropout. Beneficially, the devices and techniques described herein can be used to measure the dew point pressure as well as the volume fraction of dropout as a function of temperature and pressure.

A beam of light reflecting from a smooth surface will primarily be reflected such that the light intensity is concentrated in a beam where the incident and reflecting angles are equal. It is well-known that a roughened surface will induce a large degree of optical scattering such that a large portion of the reflected light will be scattered about a $2\pi$ solid angle. Deposition of dew or other fluid on such a rough surface effectively reduces the surface roughness by filling in pores and pits. Recognizing this, differences in reflectivity can be used along with appropriate illumination and detection sources, to detect the deposition of dew.

As used herein, the term rough or roughness in relation to surfaces includes micro-faceted or micro-patterned surfaces, such as surfaces modified to include structured patterns of features. Such features can include holes and rods, such as those described in the illustrative examples. It is understood that cross sectional shapes of any such holes or rods can be regular shapes, such as polygons and ellipses, irregular shapes, or some combination of regular and irregular shapes. Alternatively or in addition, the depths of such holes and heights of such rods can be regular (e.g., constant), or irregular (e.g., variable). The particular arrangements of such surface features, can be regular (i.e., periodic), irregular (i.e., aperiodic), and in at least some embodiments, random.

The difference in optical qualities can be discerned by an appropriate optical source and detector that are positioned to detect the change in reflectivity of the substrate. In what follows, details of the fabrication and detection process are discussed as well as ways to determine the dew composition and induce preferential wetting by alkanes. As also discussed are other techniques, such as fluorescence and tailoring of the surface properties can be used to assist in determining the composition of the condensed fluid. For example, differences in one or more of fluorescence response and surface wettability (e.g., the patterned structures wetting better for oils than water) can be used to distinguish between water and oily compounds.

Figure 2A:
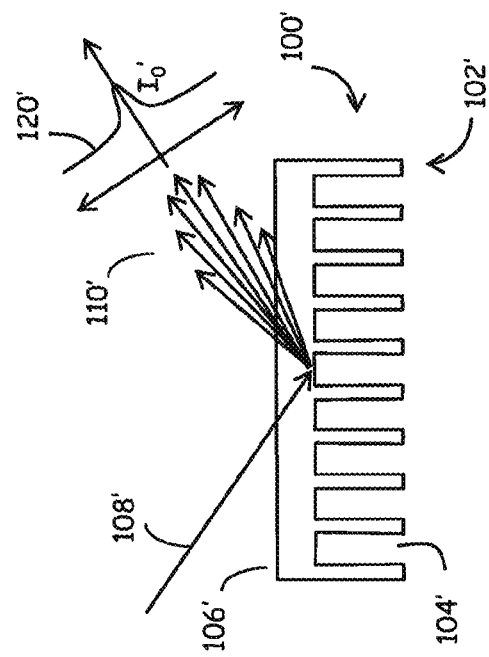
FIG. 2A shows a ray tracing diagram of a cross section of an embodiment of a patterned structure without condensate.

Referring to FIG. 2A a ray tracing diagram is shown of a cross section of an embodiment of a patterned structure 100 without condensate. The patterned structure 100 includes a roughened surface 102 including an open volume 104 accessible by the roughened surface. In the illustrative embodiment, the patterned structure 100 is substantially planar, with the roughened surface 102 disposed along one side and a smooth surface 106 disposed along an opposite side. As shown, illumination 108 incident upon the roughened surface 102 generally scatters as a result of the roughened surface 102. An optical intensity is shown along a ray corresponding to an angle of reflection for the incident illumination 108. The scattered illumination has a value of $I_0$ along the direction corresponding generally to a direction of a reflected ray, if such a reflected ray were present.

Figure 2B:
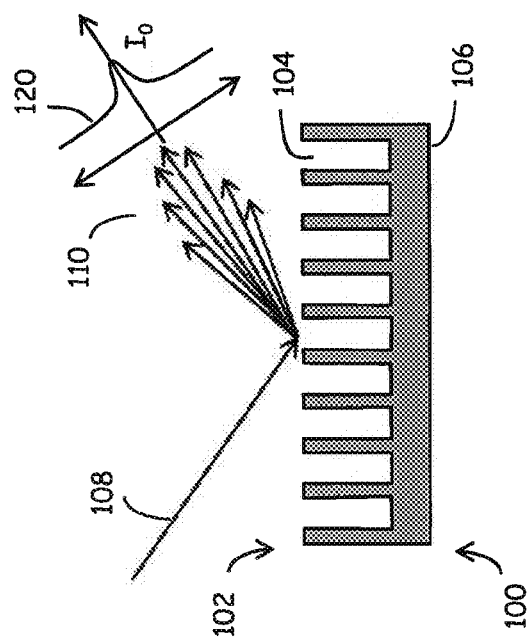
FIG. 2B shows a ray tracing diagram of a cross section of the patterned structure shown in FIG. 2A, with condensate.

Referring next to FIG. 2B a ray tracing diagram is shown of a cross section of the patterned structure shown in FIG. 2A, with condensate 114. As shown, the volume of condensate 114 is sufficient to substantially fill the open volume 104 of the roughened surface 102. As shown, illumination 108 incident upon the roughened surface 102, now filled with condensate, will generally reflect as the roughened surface 102 is effectively smoothed by the condensate 114. An optical intensity is shown along a ray corresponding to the angle of reflection for the incident illumination 108.

The reflected illumination has an intensity of $I_1$ along the direction corresponding to the reflected ray. As illustrated, the intensity $I_1$ along the reflected ray of the patterned structure 100 filled with condensate 114 is substantially greater than the intensity $I_0$ along the same angle for the patterned structure 100 without condensate 114. Also illustrated, off-axis intensity 120 without condensate 114 is greater than off-axis intensity 122 with condensate 114, due to scattering at the roughened surface 102. Thus, illumination either along the reflected ray or offset from the reflected ray can be used as an indicator of condensate.

Figure 3A:
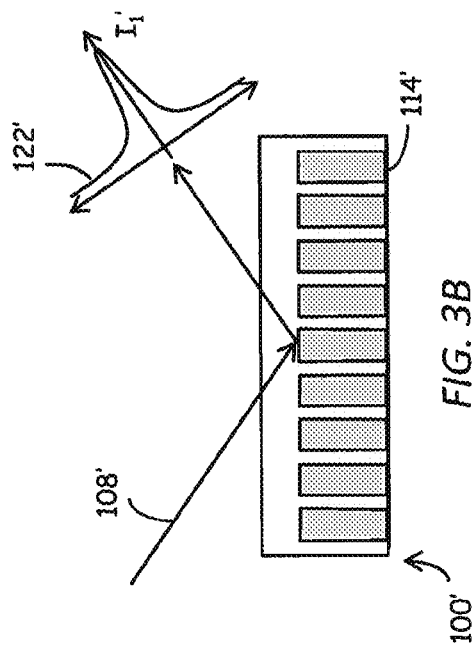
FIG. 3A shows a ray tracing diagram of a cross section of another embodiment of a patterned structure without condensate.

A ray tracing diagram of a cross section of another embodiment of a patterned structure without condensate is shown in FIG. 3A. The patterned structure 100' includes a roughened surface 102' including an open volume 104' accessible by the roughened surface 102'. In the illustrative embodiment, the patterned structure 100' is substantially planar, with the roughened surface 102' disposed along one side and a smooth surface 106' disposed along an opposite side. In this embodiment, the patterned structure 100' is optically transparent. As shown, at least a portion of illumination 108 incident upon the smooth surface 106' (e.g., a rear surface) enters the optically transparent medium and encounter the roughened surface 102, which results in scattered light 110'. At least a portion of the scattered light 110' travels back through the optically transparent medium and exits from the smooth surface 106'. An optical intensity is shown along a ray corresponding to an angle of reflection for the incident illumination 108. The scattered illumination has a value of $I_0'$ along the direction corresponding to a reflected ray. In at least some embodiments, the incident illumination 108' encounters the smooth surface 106' at an angle, such as its Brewster angle, thereby avoiding reflection from the smooth surface 106'.

Figure 3B:
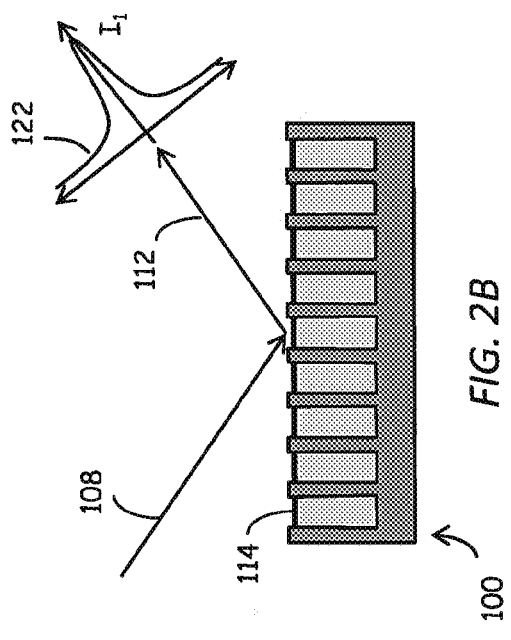
FIG. 3B shows a ray tracing diagram of a cross section of the patterned structure shown in FIG. 3A, with condensate.

Shown in FIG. 3B is a ray tracing diagram of a cross section of the patterned structure shown in FIG. 3A, with condensate. As shown, the condensate 114' substantially fills the open volume 104' of the roughened surface 102'. As shown, illumination 108 incident upon the roughened surface 102', now filled with condensate, will generally reflect as the roughened surface 102' is smoothed by the condensate 114'. An optical intensity is shown along a ray corresponding to the angle of reflection for the incident illumination 108.

The reflected illumination has an intensity of $I_1'$ along the direction corresponding to the reflected ray. As illustrated, the intensity $I_1'$ along the reflected ray of the patterned structure 100' filled with condensate 114' is substantially greater than the intensity $I_0'$ along the reflected ray of the patterned structure 100' without condensate 114'. Also illustrated, off-axis intensity 120' without condensate 114' is greater than off-axis intensity 122' with condensate 114', due to scattering at the roughened surface 102'. Illumination of partially filled wells (or voids between rods), even if back illuminated, results in an intensity returned from the patterned structure 100' that is somewhere between $I_0'$ and $I_1'$. As the variation of intensity with volume fraction is generally monotonic between these values, though not necessarily linear, a reliable interpretation of the volume fraction can be obtained.

Figure 4:
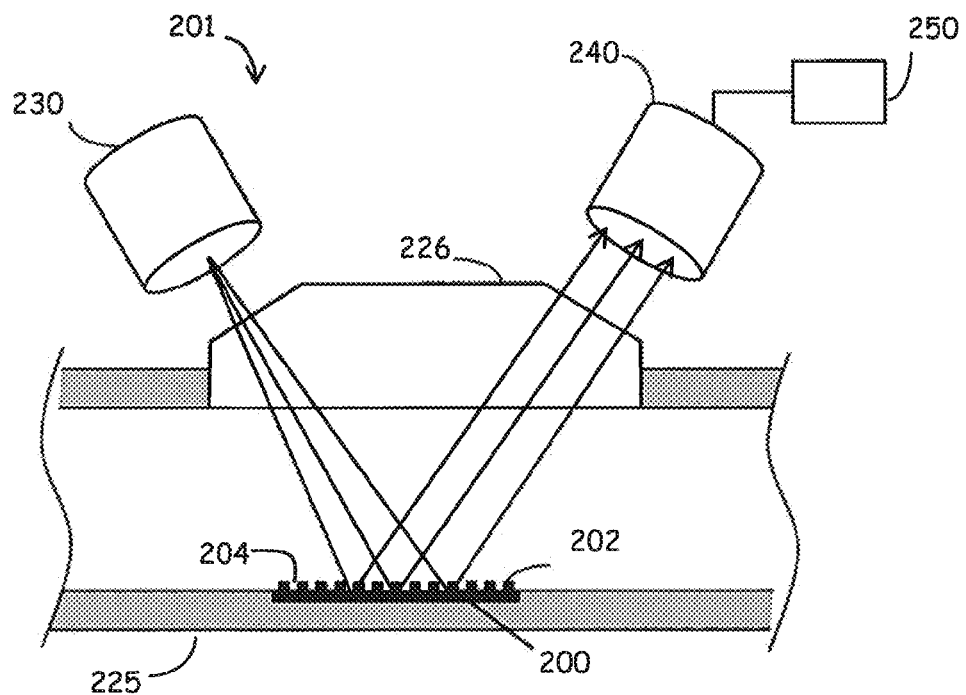
FIG. 4 shows a schematic diagram of a cross section of a sample chamber including an embodiment of a condensate detector.

Referring to FIG. 4 a schematic diagram is shown of a cross section of a sample chamber including an embodiment of a condensate detector 201. The gaseous sample chamber 200 is shown in part. It is understood that in at least some of the embodiments described herein, the sample chamber 200 is sealable, such that a sampled volume of gas can be sealed off from an external environment. Also not shown, any of the sample chambers described herein can be configured to provide a variable volume as can be used in varying pressure of a gas sample. Such volumetric variation can be accomplished by techniques known to those skilled in the art, such as including one or more piston chambers open to the gaseous sample chamber 225.

In the illustrated embodiments, a patterned structure 200 is provided having a roughened surface 202 that includes an open volume 204 accessible by the roughened surface 202. The patterned structure is disposed within the gaseous sample chamber 225, such that the roughened surface is exposed to an interior volume of the chamber 225. For example, the patterned structure 200 can be attached to or otherwise integrated in a wall of the sample chamber 225.

In at least some embodiments, a window 226 is included to allow external optical access to the interior sample volume of the sample chamber 225. In at least some embodiments, the window 226 is substantially transparent at wavelengths of interest. In particular, the window 226 is positioned to allow external viewing of at least a portion of the roughened surface 202. The window can be any suitable material, such as acrylic, glass and crystal. In the example embodiment intended for downhole applications, one or more of the temperatures and pressures can be substantially elevated over surface ambients, e.g., temperatures up to 100° C., 150° C., or 200° C. and higher and pressures up to 500 psi, 1,000 psi, 10,000 psi, 30,000 psi and higher. One such window material able to withstand such temperatures without failure or discoloration is sapphire.

An illumination source 230 is provided external to the sample chamber and positioned to illuminate at least a portion of the roughened surface 202 through the window 226. In some embodiments, the illumination source 230 is broad spectrum, for example, providing a substantially white light (e.g., a lamp). Alternatively or in addition, the illumination source may be relatively narrow spectrum device, emitting light within a relatively restricted wavelength band. For example, the illumination source 230 can be one or more of an incoherent source, such as an incandescent source, a gas discharge source (e.g., fluorescent), a solid state source (e.g., light emitting diode (LED)). Alternatively or in addition, the illumination source 230 can include a coherent source, such as a laser (e.g., a semiconductor laser).

The condensate detector 201 also includes a light detector 240. The light detector 240 is positioned to detect light from the illumination source 230 after having interacted with the patterned structure 200. In the example embodiment, the light detector 240 is positioned to detect light reflected from the roughened surface 202. In particular, the light detector is also positioned external to the sample chamber, such that light reflected and/or scattered from the roughened surface 202 traverses the window 226, exiting the sample chamber 225 before detection. Although the various embodiments described herein incorporate at least one window allowing illumination sources and detectors to be located outside of the sample chamber, it is conceivable that one or more of the sources and detectors can be located within the sample chamber, thereby eliminating the need for a window.

In any of the arrangements describe herein and equivalents thereto, the light detector 240 can be positioned and otherwise arranged to detect illumination along a ray from the source 230, reflected by the surface 202. Detection of a relatively large illumination value in such configurations is indicative of little or no scattering, whereas detection of a relatively small illumination value is indicative of scattering. Alternatively or in addition, the light detector 240 can be positioned and otherwise arranged to detect illumination at a position offset from such a reflected ray. Conversely, detection of a relatively large illumination value in such configurations is indicative of scattering, whereas detection of a relatively small illumination value is indicative of little or no scattering.

Any suitable light detector 240 can be used. For example, the detector can include a photodiode, an avalanche photodiode, a phototransistor, a photomultiplier tube, a photovoltaic cell, photo resistor, a charge-coupled device (CCD) and the like. Generally, the particular light detector 240 is detected according to the application, including the illumination source 230. For example, in some embodiments, the light detector 240 can provide a relatively broad spectrum optical response as may be advantageous for a white light illumination source 226. Alternatively or in addition, the light detector 240 can provide a relatively narrow spectrum optical response as may be advantageous in providing a wavelength dependent detection of light.

When illuminated by white light at a fixed angle, the periodicity of the micro-textured pattern of the roughened surface, leads to certain wavelengths being constructively interfered. This is different than the reflection by the surface over all wavelengths discussed above. Such constructive interference should be stronger, for example, in the absence of condensation and weaken as a fluid is condensed and begins to fill the voids. Thus a change in a wavelength dependent response can be used as an alternative mode for detecting dew. For example, a measured response of reflected light versus wavelength may show one or more relatively narrow minima associated with the particulars of the pattern (e.g., hole/post size, shape, array spacing, depth/height). In at least some embodiments, the measure response is indicative of a Fourier transform of one or more of the underlying periodicity and spacing of the surface features, the surface features effectively modulating impingent illumination. As the roughened surface is wetted by dew, the relatively narrow minima may change in one or more of height and width, and ultimately disappear when the patterned structure is filled completely. The relative intensity of detected illumination returned from the surface generally decreases with increasing liquid levels wetting the surface, except for the 0,0 peak (i.e., pure reflection), which increases.

Figure 5:
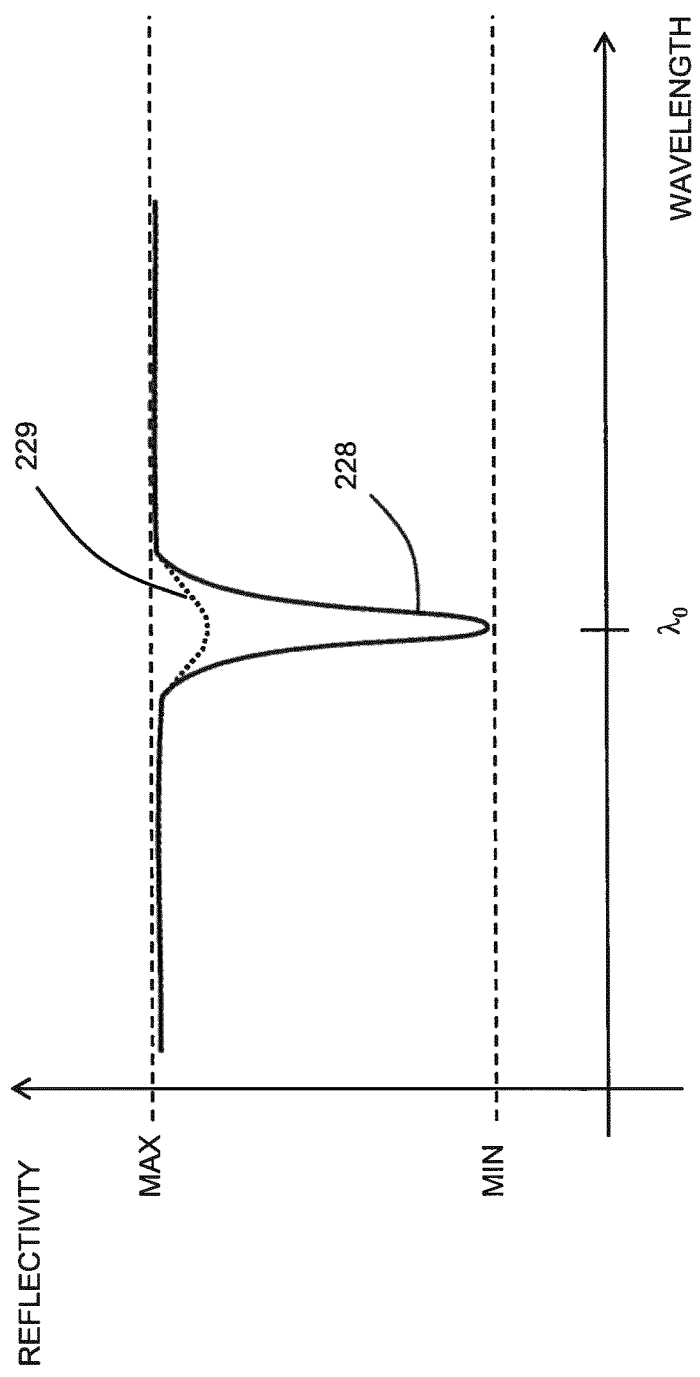
FIG. 5 shows a representative graph of reflectivity of an embodiment of a roughened surface when empty versus when at least partially filled with a condensate.

An example graph of reflectivity versus wavelength is shown in FIG. 5 for an embodiment of a roughened surface. For a patterned surface having holes for surface features, the reflectivity is generally high for most wavelengths. However, for at least a narrow band of wavelengths $\lambda_0$, constructive and destructive interference resulting from the surface features results in a dramatic reduction in the reflectivity 228, to some minimum value. When the features are otherwise filed (i.e., the holes or voids between are filled rods by condensate), the sharp reduction in reflectivity 228 is reduce 229 if not substantially eliminated. Thus, measurement of illumination in and around $\lambda_0$ can be used as an indicator of dew dropout.

It is conceivable that optics (not shown) can be employed between the illumination source 230 and the light detector 240. For example, a collimating lens can be employed to collimate light from the illumination source 230, such that collimated light is incident upon the roughened surface 202. Alternatively or in addition, imaging optics can be similarly employed between one or more of the illumination source 230 and the light detector 240, for example to focus illumination on a particular region of the roughened surface 202 to image the roughened surface 202 upon the light detector 240, or some combination of both. Such optics can be used with any of the embodiments described herein and equivalents thereof The condensate detector 201 includes a detection processor 250 in communication with the light detector 240. In at least some embodiments, the detection processor 250 is configured to determine one or more of a presence or absence of a condensate at the patterned structure 200. For example, the detection processor 250 can compare a detector output to a threshold, concluding the presence or absence of a condensate according to the comparison. The detection processor 250 can be configured to execute one or more processes according to preprogrammed instructions stored within memory and available to the processor 250. In some embodiments, the detection processor 250 can include a signal analyzer. One or more of the processing steps described herein can be implemented within the detection processor 250, which may include one or more of a general purpose computer, a specific programmed processor, hardware (e.g., elements configured to implement digital signal processing), firmware and combinations of such devices.

In at least some embodiments, the detection processor 250 is coupled to one or more additional elements of the condensate detector 201. For example, the processor 250 can be in communication with the illumination source 230, controlling one or more of intensity, duration, etc. Alternatively or in addition, the processor 250 can be in communication with features of the gaseous sampling chamber 225, such as valves (not shown) to control acquisition and retention of a gaseous sample, pistons (not shown) to control volumetric variations of the interior volume of the chamber 225, and temperature control elements as will be discussed in more detail below.

At least one disadvantage of the previous examples is that illumination from the illumination source 230 must pass the gaseous chamber 225 twice before it is detected. As the chamber 225 will likely include a single phase (e.g., gaseous), or perhaps multi-phase sample during operation, there is a possibility that the sample will impede with obtaining any measurements. For example, the gaseous sample may result in one or more of absorption and scattering of the illumination, perhaps leading to reduced efficiency, reduced sensitivity and possibly reduced accuracy, depending upon the nature of any such interaction.

During a dew point measurement one typically starts with a high pressure cell full of a single phase, gaseous mixture. The micro-textured surface is placed in the cell such that at early time the surface appears quite rough. This surface can be illuminated through an optical window with a broad band or single wavelength light source. Upon decreasing the pressure, dew condenses and is wicked into the pores and pits on the roughened surfaces of the patterned structures due to capillary action. By effectively reducing the roughness of the surface, the presence of dew changes the surface's optical properties. Condensation at the typical pressures seen downhole involves a density increase from the gaseous to liquid phase of roughly a factor of two to four. In some cases, the dew dropout volume fraction can be as high as one third. Hence to capture the dew, a cell can be designed such that for every 1 part liquid dropout volume (e.g., contained in the micro-textured surface), there are 2 parts gaseous volume, ideally in the space next to the micro-textured surface. Those skilled in the art will realize that the pressure need be changed by at least 30% to induce dew drop out for typical oilfield samples.

In operation, light from the illumination source 230 is either scattered, reflected, or some combination of scattered and reflected by the patterned structure 200, depending upon the presence of dew dropout. When no dew dropout is present, and particularly when the patterned structure 200 is not wet (i.e., substantially no liquid within the open spaces 204), the roughened surface 202 appears rough and scatters the incident illumination. As a consequence, a relatively low intensity ($I_0$) portion of the scattered light detected by the light detector 240. Alternatively, when dew dropout is present and with the roughened surface 202 of the patterned structure 200 is substantially filled with fluid, the roughened surface 202 appears relatively smooth. Thus, a substantial portion of incident light from the illumination source 230 is reflected from the surface 202. As a consequence, a relatively high intensity ($I_1 > I_0$) portion of the scattered light detected by the light detector 240. In alternative embodiments the detector can be positioned to detect scattered light (e.g., being off axis with respect to a reflected ray). In such embodiments, an absence of dew would result in a relatively high intensity ($I_0$); whereas, presence of dew would result in a relatively low intensity ($I_1 < I_0$). In some embodiments, multiple detectors can be provided to preferentially detect one or more of reflected and scattered illumination.

Figure 6:
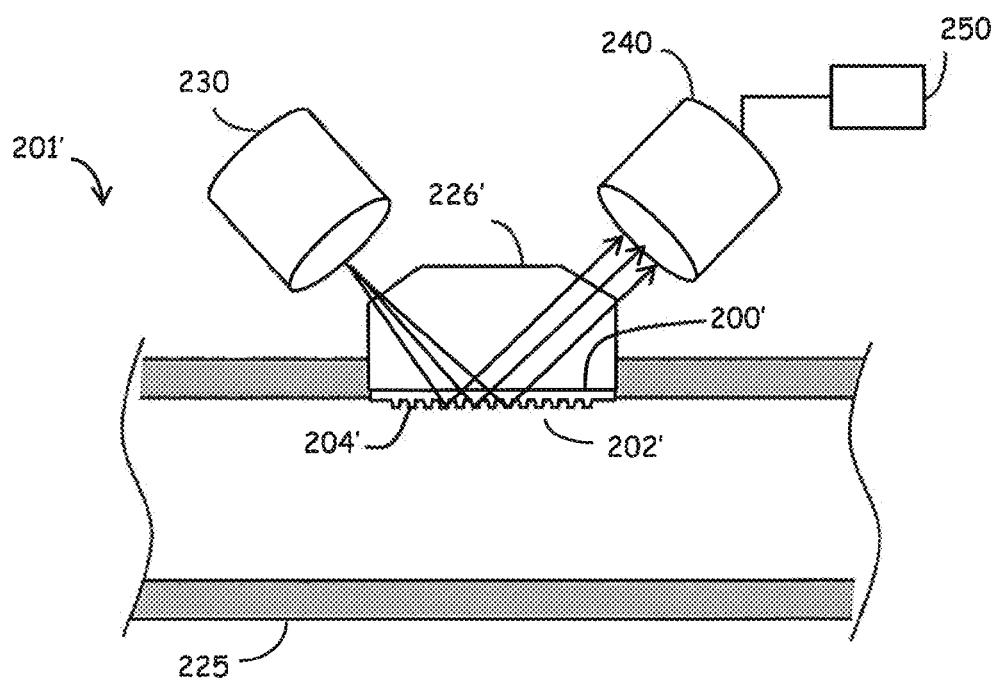
FIG. 6 shows a schematic diagram of a cross section of a sample chamber including another embodiment of a condensate detector.

Referring to FIG. 6 a schematic diagram is shown of a cross section of an alternative embodiment of a condensate detector 201' that enables interrogation of a patterned structure 200' by the external illumination source 230, without requiring the illumination to traverse the chamber 225. In particular, the chamber 225 includes a window 226' having an interior-facing surface exposed to an interior volume of the sample chamber 225 and a patterned structure 200' mounted along the interior surface of the window 226'. As in the previous examples, the patterned structure 200' includes a roughened surface 202' including an open volume 204' accessible by the roughened surface 202'. The patterned structure 200', however, is substantially transparent allowing illumination from the illumination source 230 to pass through the window 226' and through the patterned structure 200', reaching the roughened surface 202' from a rear-facing surface (e.g., as in the examples of FIGS. 3A and 3B). In at least some embodiments, the roughened surface 202' can be etched into the interior-facing surface of the window 226' itself, thereby eliminating the need for a separate component. In operation, illumination from the illumination source 230 is returned from the patterned structure 202', through the window 226' and directed toward the detector 240. Processing of the detector output by the processor 250 can be accomplished, for example, as described above.

It has been observed that dew in many cases possesses a sufficiently large fraction of aromatics and similar molecules to fluoresce. Hence illumination of this configuration by a high energy wavelength, e.g., 400 nm, produces lower energy and hence wavelengths when the micro-textured surface is filled with the condensation of dew. This fluorescence signature generated by the condensate fluid can aid in discerning between oil or a mud-based filtrate and a formation hydrocarbon. It is understood that substantially all downhole fluids possess a certain level of fluorescence due to either aromatics or asphaltenes in the hydrocarbon phase or surfactants in the aqueous filtrate. The relative values of the fluorescence intensity can be used to provide supplemental information to differentiate between the components.

Figure 7:
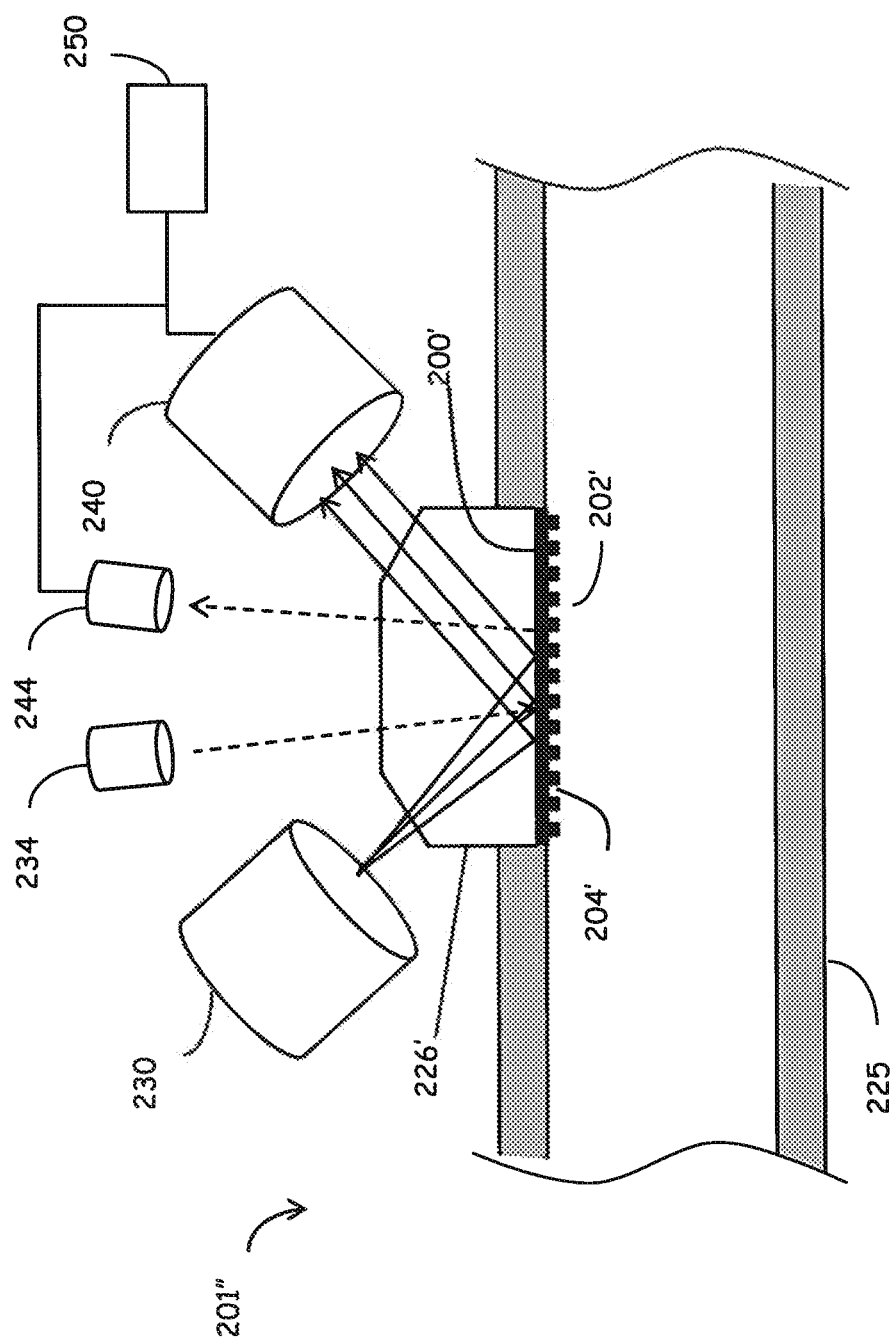
FIG. 7 shows a schematic diagram of a cross section of a sample chamber including yet another embodiment of a condensate detector configured to detect fluorescence response.

In at least some embodiments, a combination of constructive interference and fluorescence can be used to monitor the composition and measure the quantity of dew. Referring to FIG. 7 a schematic diagram is shown of a cross section of a sample chamber 225 including another embodiment of a condensate detector 201". The detector 201" includes a second illumination source 234 and at least one additional detector 244. The illumination source 234 is selected to excite target components sufficiently, such that when present, they fluoresce. The additional detector 244 is a fluorescent detector 244 adapted to detect and otherwise differentiate illumination as falling in a different wavelength band (e.g., a longer wavelength band) than the illumination source 234. Fluorescence will result when a condensate is present on the roughened surface 202'. Thus, detection of any signals by the fluorescent detector 244 is indicative of the presence of a liquid drop out.

In at least some embodiments, a second illumination source 234 is not required for detecting fluorescence, because the single source 230 can be used for this purpose. In some embodiments, the source 234 can be filtered with a short pass filter (not shown). In some embodiments, the source 234 is a short wavelength, narrow-band UV or blue emitter, such as an LED or laser diode; however, a broadband source such as a tungsten halogen filament can also be used. If the source 234 is a laser diode, a band-pass (i.e., "cleanup") filter can be used instead of, or in combination with a short pass filter. A short wavelength source 234 allows the smaller chromophores (present in higher concentrations) in the crude the oil fraction to fluoresce, maximizing the sensitivity to crude oil. In at least some embodiments, the fluorescence detector 244 can be combined with a filter, such as a long-pass filter with a cutoff at least 50 nm above (i.e., "longer") than the short pass filter cutoff wavelength.

In at least some embodiments, the reflectivity detector 240 and the fluorescence detector 244 can be utilized to distinguish between water, oil and gas. For example, if the source 230 and detector 240 are positioned at a 45 degree angles with respect to the surface normal (i.e., 90 degrees apart), and the window 226 is a sapphire material, then the detector 240 shows a high reading for gas but a low reading for oil and water, whereas the fluorescence detector 244 records a high signal only when oil is present. If water is present, both detectors 240 and 244 produce a low signal. In some embodiments, for example depending upon intensity of the one or more sources 230, 240, one of gas, oil and water may fluoresce, whereas one or more of the others may not. In such embodiments, detection of any fluorescence can be used as a means for distinguishing among the more than one compound. In at least some embodiments, one or more additional reflection detection channels can be utilized. For example, if the source 230 is positioned at 45 degrees (measured from surface normal), a second reflection detector can be positioned at 55 degrees (also measured from surface normal). Such a second reflection detector advantageously detects water and gas, but not oil.

In at least some embodiments, multiple frequency selective detectors 244 (e.g., with respective band pass filters) can distinguish within sub wavelength bands of the fluorescent spectrum. The detectors 244 may be used to collect more detailed information about the fluorescence spectrum, enabling discrimination between light and heavy oil fractions and/or oily water. In such embodiments, any liquid drop out portion can be identified by the characteristics of the fluorescent spectra. For example, both oily water drop out and oil drop out can fluoresce. In at least some embodiments, one or more of the illumination source 234 and fluorescent detector 244 can be controlled by the processor 250. Through difference in the fluorescent spectra, however, it is possible for the detector 244 and processor 250 to distinguish oil from oily water based on the characteristics of the fluorescent spectra.

Although the fluorescent source 234 and detector 244 are shown in combination with a particular configuration of the window 226' and patterned surface 200', it should be understood that the fluorescent source 234 and detector 244 can be used with any of the embodiment described herein including equivalent structures and techniques.

Figure 8:
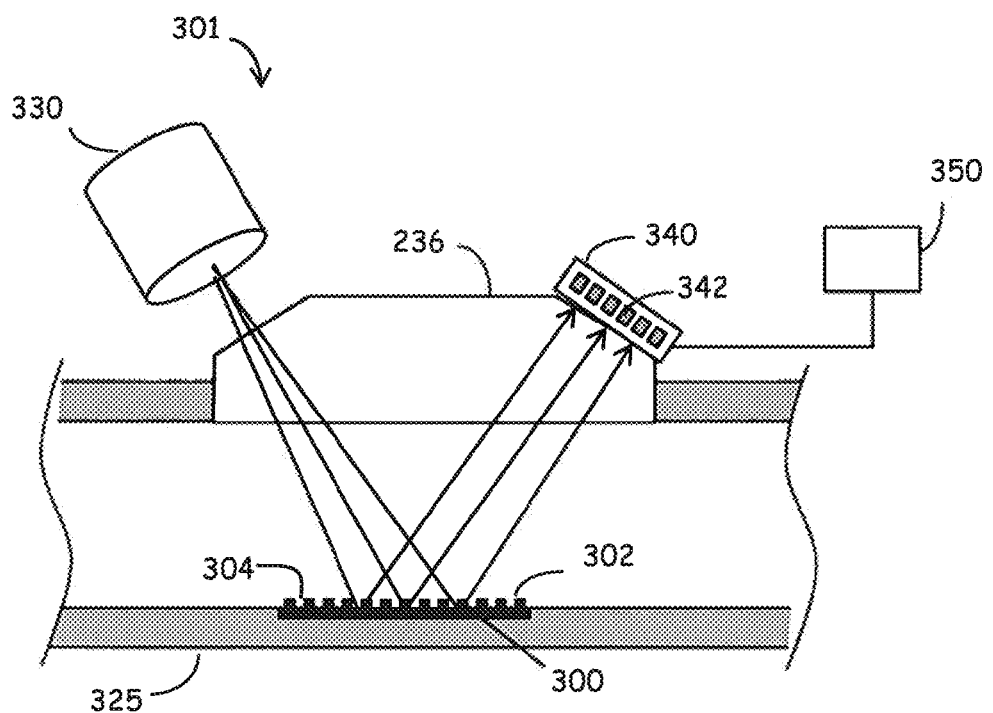
FIG. 8 shows a schematic diagram of a cross section of a sample chamber including another embodiment of a condensate detector.

Referring to FIG. 8 a schematic diagram is shown of a cross section of a sample chamber including another embodiment of a condensate detector 301. The condensate detector 301 includes a gaseous sample chamber 325, shown in part, and a patterned structure 300 having a roughened surface 302 including an open volume 304 accessible by the roughened surface 302. The patterned structure 300 is disposed within the gaseous sample chamber 325, such that the roughened surface 302 is exposed to an interior volume of the chamber 325. The condensate detector 301 also includes window 326 allowing external optical access to the interior sample volume of the sample chamber 325, along with an illumination source 330 and a light detector 340. A detection processor 350 is also provided in communication with the light detector 340.

The condensate detector 301 is similar to the embodiment shown in FIG. 4, with the exception of details related to the light detector 340. In some embodiments, the light detector 340 can be configured to independently detect in more than one different wavelengths. Such wavelength dependent detectors are commonly used in spectrographic applications. Alternatively or in addition, the light detector 340 can include an array of detector elements 342. Such a detector array 340 can include various arrangements of array elements, such as linear arrangements, circular arrangements and rectangular arrangements. In such arrangements, each array element 342 can be considered as a pixel, having at least some spatial variation from other pixel elements of the array 340. In at least some embodiments, the detector array 340 can be used to obtain an image of at least a portion of the roughened surface 320. Such detectors can include imaging detector arrays, such as CCDs and can be used with or without optics.

Figure 9:
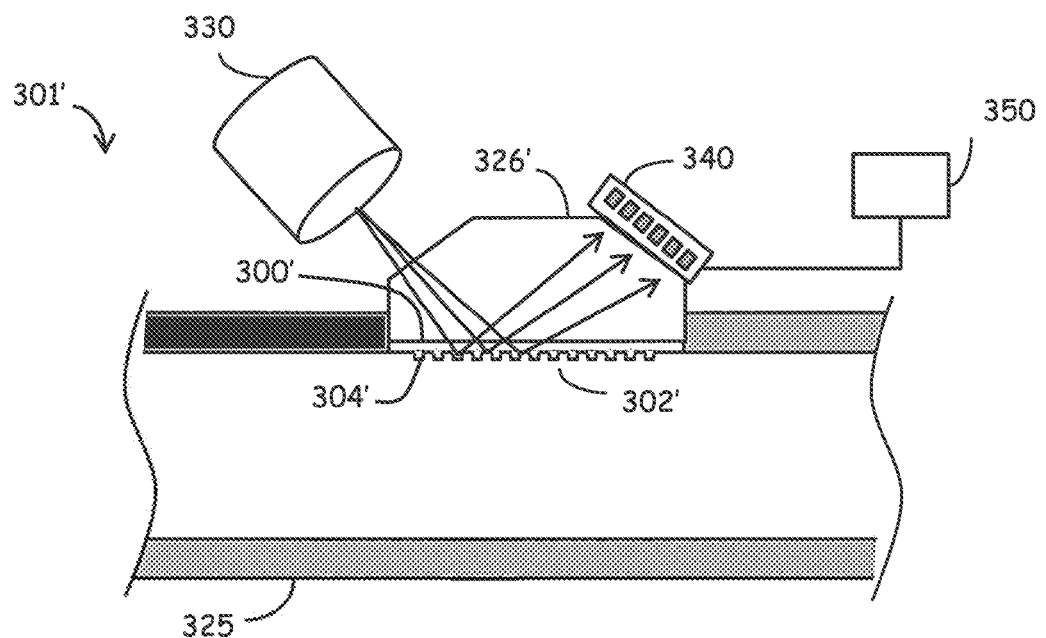
FIG. 9 shows a schematic diagram of a cross section of a sample chamber including yet another embodiment of a condensate detector.

Referring to FIG. 9 a schematic diagram is shown of a cross section of a sample chamber including yet another embodiment of a condensate detector 301'. The illustrated embodiment essentially includes the detector 340 arrangement described above in relation to FIG. 8, with a window 326' and patterned structure 300' arrangement similar to the example of FIG. 6.

Referring to FIG. 10A a perspective schematic diagram is shown of an embodiment of a patterned structure 400. The structure 400 includes a solid material 401 having at least one roughened surface 402. The illustrative example includes a planar structure, but this is by no means intended to be limiting. For example, the solid material 401 and/or the roughened surface 402 can take on various other shapes, such as angular shapes (e.g., a notch or a groove), curved shapes (e.g., a cylindrical section, a conic section, a spherical or ellipsoidal section), and combinations of such shapes. An open volume 404 can be provided by a plurality of open structures defined within the solid material 401, each having an opening along the roughened surface 402. For example, the open volume is provided by a sum of interior volumes of open structures, such as open cylindrical cavities, exposed to the sample chamber. Alternatively or in addition, the open volume can be provided by open space between surface structures, such as voids between posts or cylinders. In some embodiments, the open volume represents a measureable fraction of the interior volume of the gaseous sample chamber. For example, the open volume can be at least about 0.1%. In other embodiments, the open volume represents a greater fraction, such as at least about 1%, at least about 5% or at least 10% of an interior volume of a gaseous sample chamber in which the structure 400 is placed. In other embodiments, the open volume represents up to one quarter or one third of the total sample chamber volume.

In the illustrative example, the open structures 404 are defined by right circular cylindrical cavities 404. Each cylindrical cavity 404 has an open end along the roughened surface 402 and extends for a depth into the solid material 401. In the illustrative example, a surface opposite the roughened surface 402 is a relatively smooth surface 406. In at least some embodiments, the same open structure 404 is repeated in an array across the roughened surface 402, as shown. Such an array can be a regular array in which the open structures 404 are repeated according to a regular spacing (e.g., a grid), as shown. The material 401 can be opaque, or transparent.

Referring to FIG. 10B a cross-section is shown of the patterned surface condenser shown in FIG. 10A, taken along A-A. Each of the open cylindrical cavities 404 has an internal diameter d, and a center-to-center, or array spacing s. A thickness of material between edges of adjacent open cylinders 404 is t, which can be determined, for example, as a difference between the array spacing and diameter (i.e., t=s−d). Each of the cylindrical cavities 404 extends for a length L into the material as measured from the roughened surface 402.

Roughened surfaces 402 can be fabricated by many methods, some of which are listed herein. The fabrication processes can be roughly classified as either subtractive, whereby material is etched away from a relatively smooth surface to make a rough one, or additive, whereby structures are induced to grow on a relatively smooth surface. Subtractive processes include the following: grinding a metal surface with a particulate-laden slurry, rubbing sand paper with a well-controlled grit size, or by acid etching. The embodiment illustrated in FIG. 10A is an example of a patterned surface 402 obtained by a subtractive process. Additive processes include the growth of carbon nanotubes on surfaces or the laser ablation of surfaces to induce arrays of micro facets or asperities. The embodiment illustrated in FIG. 11A is an example of a patterned surface 402' obtained by an additive process.

An additional subtractive process that affords exquisite control is micro-fabrication. The fabrication techniques used to create integrated chips or microchips allow one to etch silicon wafers with micron-scale precision. For example, it is well-known how to fabricate 10 micron holes in a silicon wafer with a depth of 200 microns to those skilled in the art. An array of such holes can be fabricated to appear as the micro-textured structure in FIG. 10A. These holes act as arrays of capillaries to induce fluid (i.e., dew) to be transported by surface tension to the bottom of the capillary with a wicking action. By choosing appropriate lattice constants and hole diameters the void fraction, or empty space, of a micro-fabricated chip could be as high, or even higher, than 50%.

Referring to FIG. 11A a perspective schematic diagram is shown of another embodiment of a patterned structure 400'. This embodiment is complementary to the previous example, in that the roughened surface 402' includes a multitude of right circular cylinders or posts 408 extending away from a base portion of the material 401'. Each of the cylinders 404' has a diameter d and is spaced apart from neighboring cylinders 408 by a separation distance t. The open space or void 404' is defined by the space defined in between the protruding cylinders 408. Referring to FIG. 11B, a cross-section is shown of the patterned surface structure 400' shown in FIG. 11A, taken along B-B. Also shown is a fluid 410 partially wetting the patterned structure 400.' In such a partially wetted state, at least the tip portions of some of the posts 408 extend above a surface of the fluid 410. Accordingly, the roughened surface 402' retains at least some roughness.

Sensing the condensation of dew with a sensor of small thermal mass facilitates ease of thermal manipulation. For example, surface heaters can be easily integrated onto the micro-textured surface and the application of a small amount of power can rapidly raise the temperature of the surface. Alternatively, Peltier or thermoelectric type coolers can be used to cool the surface. Alternatively or in addition, the micro-textured surface can be further isolated thermally by mounting it on posts so as to accelerate its thermal manipulation.

Figure 12:
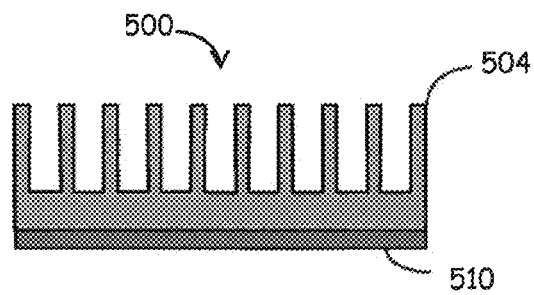
FIG. 12 shows a cross-section of an embodiment of a thermally adjustable patterned structure.

Referring to FIG. 12 a cross-section is shown of an embodiment of a thermally adjustable patterned structure 500. The thermally adjustable patterned structure 500 includes a patterned structure 505 and a thermal element 510. The composition of the patterned structure 505 can be any of the various configurations and material describe herein. The thermal element 510 can be a heating element, such as a resistive heating element, or a thermoelectric element, such as a Peltier device capable of one or more of heating or cooling. The thermal element 510 is in thermal communication with the patterned structure 505. Such modes of thermal communication can include one or more of conduction, convection and radiant heat transfer. In the illustrative example, the thermal element 510 is provided in contact with a smooth surface of the patterned structure 505. In some embodiments, one or more additional components or compounds such as thermally conducting paste can be applied to enhance transfer of thermal energy between the patterned structure and the thermal element 510.

For most thermodynamic systems that exhibit condensation, the application of heat can be used to evaporate the dew allowing the dew point measurement to be repeated. The repeatability of this measurement is a desirable and gives the user confidence in the results. Additionally, the ability to rapidly explore a wide range of temperatures allows a user to map out a phase diagram. This is in contrast with most PVT (pressure-volume-temperature) systems in which temperature changes are either impractical or sufficiently time-consuming such that no more than two or three temperatures are explored, thereby producing a very crude phase diagram.

In at least some embodiments, the thermal element 510 is in communication with the detection processor 250, 350. The detection processor 250, 350 can operate according to pre-programmed instructions to thermally cycle the thermal element 510, for example, to evaporate condensate at the conclusion of an evaluation, allowing subsequent evaluations to take place, without contamination from any earlier evaluations.

Figure 13:
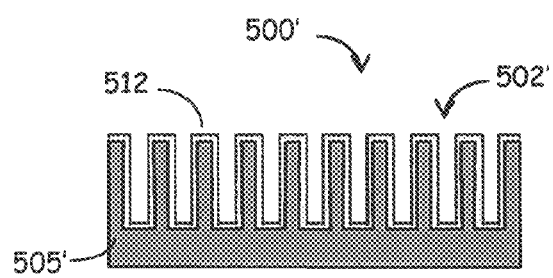
FIG. 13 shows a cross-section of an embodiment of a condensate selective patterned structure.

One of the challenges in accurately measuring a dew point of a gaseous sample is an ability to discriminate from dew that originates from contamination and the dew that originates from the formation gas and hence corresponds to the desired hydrocarbon dew point. To address this challenge, the sensor can use two surfaces: one highly hydrophobic, one relatively hydrophilic. Referring to FIG. 13, a cross-section is shown of an embodiment of a condensate-selective patterned structure 500'. The condensate-selective patterned structure 500' includes a patterned structure 505' onto which a coating 512 is applied. The composition of the patterned structure 505' can be any of the various configurations and material describe herein (e.g., holes, posts). The coating 512 can include a condensate-selective material, for example being hydrophobic or hydrophilic. A hydrophobic coating 512 preferentially inhibits wetting of the roughened surface 502' by water-based solutions. Preferably, such a hydrophobic coating does not interfere with or otherwise discourage wetting of the roughened surfaced 502' by non-water-based solutions, such as oils. In such a configuration, the patterned structure 500' selectively responds to oil-based dew dropout, without substantially responding to dew drop out of any water contaminates. Examples of hydrophobic coatings include polytetrafluoroethylene, and poly(ether ether ketone). In response to water condensate, the micro-textured pattern (lattice spacing several microns) result in water droplets that span several posts (holes) without otherwise wetting a micro-textured and hydrophobic surface. Namely, the water does not enter the open volume of the patterned structure 505'.

Likewise, a hydrophilic coating 512 preferentially promotes wetting of the roughened surface 502' by water-based solutions. Preferably, such a hydrophilic coating does not interfere with or otherwise discourage wetting of the roughened surfaced 502' by non-water-based solutions, such as oils. In such a configuration, the patterned structure 500' selectively responds to water-based dew dropout. Examples of hydrophilic coatings include reactive silicones and oxide compounds, such as titanium dioxide, aluminum oxide or silicon dioxide.

The surface chemistry can be modified by deposition of a thin (e.g., less than about 1 micron thick) layer of material, for example, after micro-fabrication of the micro-textured surfaces. Deposition can be undertaken, for example, by spin coating or plasma deposition or similar technique. For example, by spin coating a hydrophobic material, such as TEFLON AF®, the surface can be induced to be highly hydrophobic. This reduces the tendency of water to condense out onto the micro-textured surface while at the same time encouraging the alkane molecules to cover the surface. By monitoring the amount of dew on the surfaces, the type of fluid that has condensed can be deduced.

Figure 14:
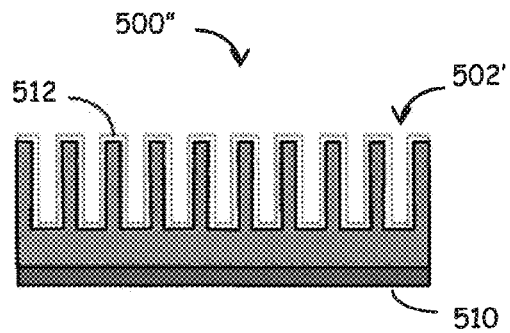
FIG. 14 shows a cross-section of an embodiment of a thermally adjustable and condensate selective patterned structure.

Referring to FIG. 14 a cross-section is shown of an embodiment of a thermally adjustable and condensate-selective patterned structure 500". The structure combines one or more features of the thermally adjustable patterned structure 500 of FIG. 12 with the condensate-selective patterned structure 500' of FIG. 13.

Figure 15:
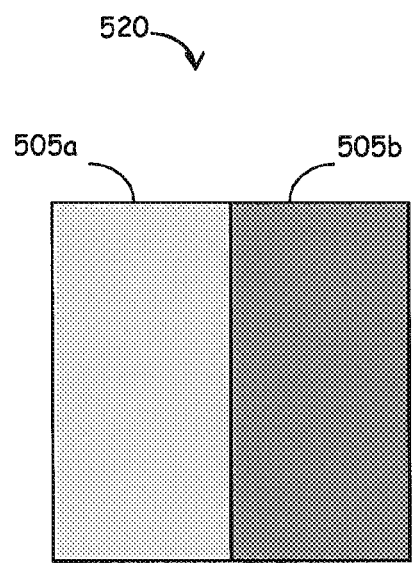
FIG. 15 shows a planar view of an embodiment of a composite patterned structure.

Referring to FIG. 15 a planar view is shown of an embodiment of a composite patterned structure 520. The composite structure 500" includes a structure including more than one different sub-structures 505a, 505b. For example, the first substructure 505a can be a hydrophilic coated structure, whereas, the second substructure 505b can be a hydrophobic coated structure. Alternatively or in addition, the substructures may vary by one or more of configuration (e.g., holes and posts), by sizes, shapes, arrangements, compositional material (e.g., clear and opaque), and the like.

Figure 16:
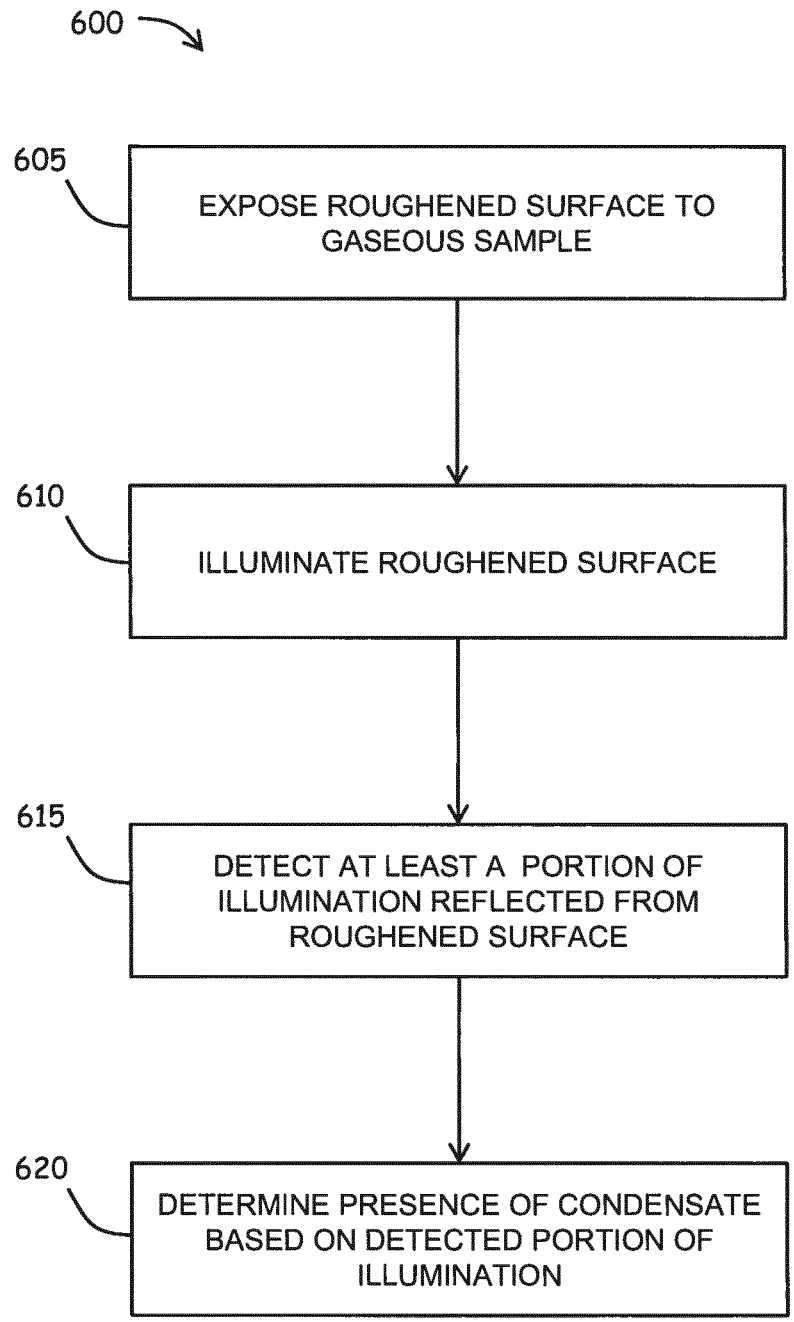
FIG. 16 shows a flow diagram for an embodiment of a process for detecting a condensate.

Referring to FIG. 16 a flow diagram is shown for an embodiment of a process 600 for detecting a condensate. A roughened surface is exposed at 605 to gaseous sample. The roughened surface is illuminated at 610. At least a portion of illumination reflected from roughened surface is detected at 615. Alternatively or in addition, at least a portion of illumination scattered from roughened surface is detected at 615. A presence of condensate is determined at 620 responsive to a detected portion of illumination.

Figure 17:
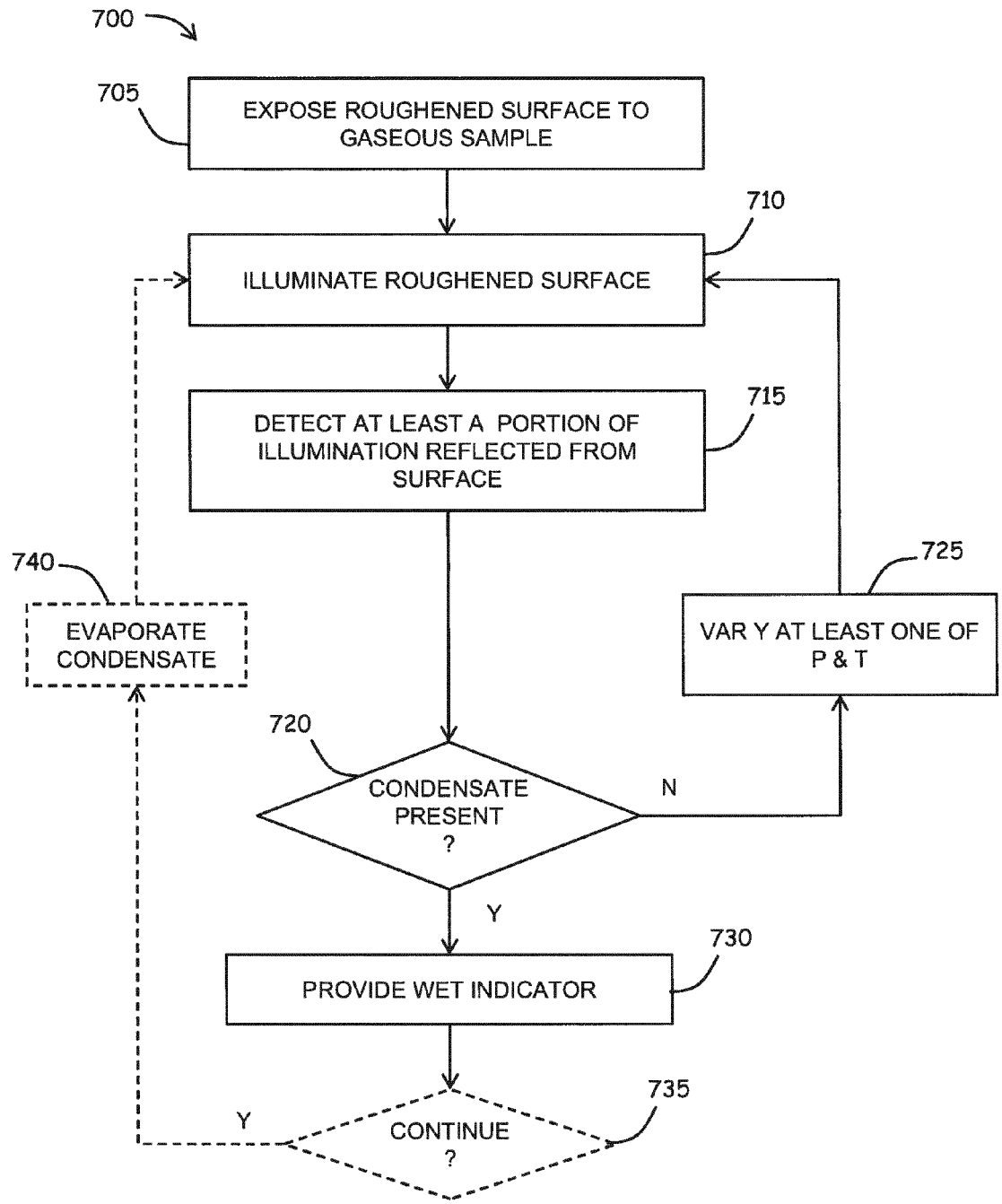
FIG. 17 shows a flow diagram for another embodiment of a process for detecting a condensate.

Referring to FIG. 17 a flow diagram is shown for another embodiment of a process 700 for detecting one of a dew point and a volume fraction dropout for a gaseous sample. The process 700 includes exposing a roughened surface to gaseous sample at 705 at a starting temperature and pressure. The roughened surface is illuminated at 710. At least a portion of illumination reflected from roughened surface is detected at 715. Alternatively or in addition, at least a portion of illumination scattered from roughened surface is detected at 715. A presence of condensate is determined at 720 responsive to a detected portion of illumination.

In at least some embodiments, if a condensate is not detected at 715, at least one of a pressure and a temperature are adjusted, for example, according to the various techniques described herein. The acts of exposing (705), illuminating (710) and detecting (715) are repeated at the adjusted temperature and/or pressure. The process can continue for other temperatures and pressures until a condensate is detected. Once a condensate is detected at 720, a wet indicator can be provided at 730. In at least some embodiments, a thermal element is actuated, for example, in response to the wet indicator, to evaporate condensate from the patterned structure thereby allowing the process to repeat. For example, the process can be repeated for various pressure and temperature programs to effectively determine at least a portion of a phase diagram for the gaseous sample being evaluated.

In at least some embodiments, the of exposing (705), illuminating (710) and detecting (715) are repeated with the act of detecting a condensate, replaced with detecting a predetermined volume of a condensate. A predetermined volume can be estimated when the roughened surface appears to be substantially smooth, indicating that any open volume is substantially filled. Since the open volume of a patterned structure can be determined beforehand (e.g., by calculation and/or testing), the volume of dew necessary to fill the open volume is known. Also having knowledge of the interior volume of the sample chamber, allows for calculation of the volume fraction dew dropout.

Figure 18A:
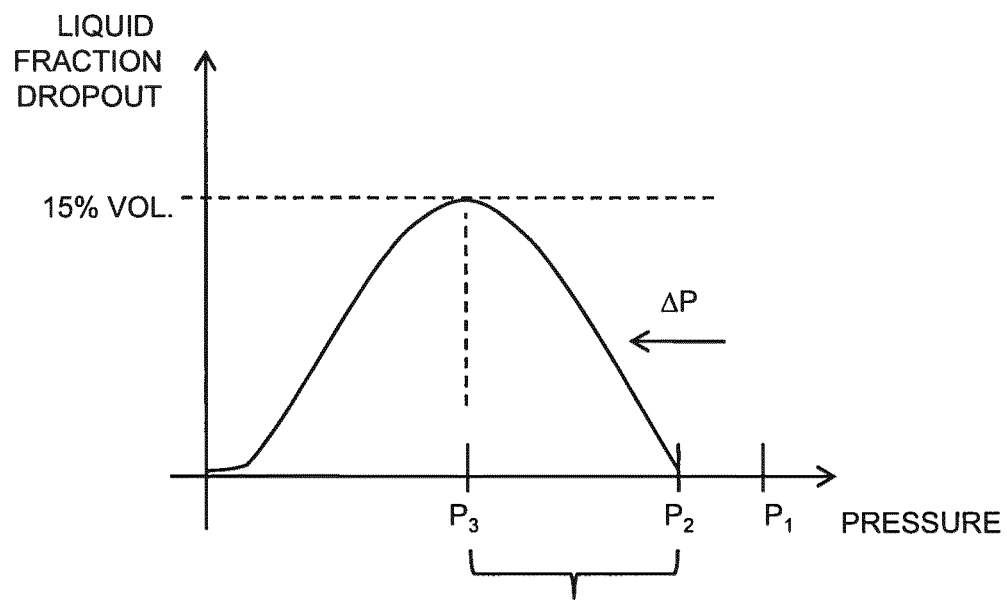
FIG. 18A shows a graph of liquid fraction dropout versus pressure for a fluid sample.
Figure 18B:
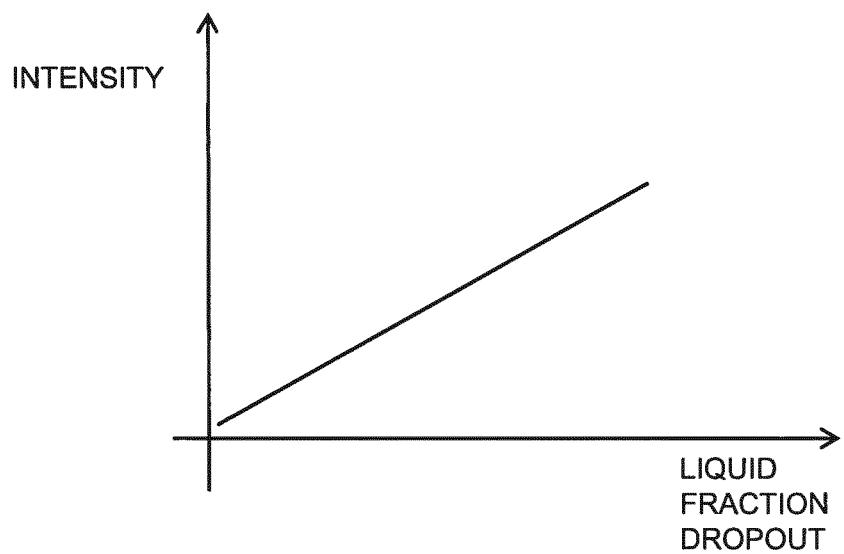
FIG. 18B shows a graph of intensity returned from an embodiment of a roughened surface exposed to the fluid sample during the pressure changes illustrated in FIG. 18A.

A representative graph of liquid fraction dropout versus pressure for a gaseous fluid sample is shown in FIG. 18A. The sample is contained within a sample chamber at a relatively high pressure $P_1$. In the illustrative example, the relatively high pressure is above a threshold pressure $P_2$ (e.g., 3K psi) at which condensation of the sample occurs. At pressures above $P_2$, the sample is substantially gaseous phase, with an insignificant the liquid fraction dropout. As pressure of the sample is reduced, for example, by increasing a volume of the sample chamber, the pressure drops below $P_2$. As the pressure continues to drop, a liquid fraction dropout increases until at some pressure $P_3$ the liquid fraction dropout reaches a maximum value. FIG. 18B shows a graph of intensity returned from an embodiment of a roughened surface exposed to the fluid sample during the reduction of pressure (i.e., between $P_2$ and $P_3$) described above. As indicated, the intensity increases monotonically, though not necessarily linearly.

Figure 19:
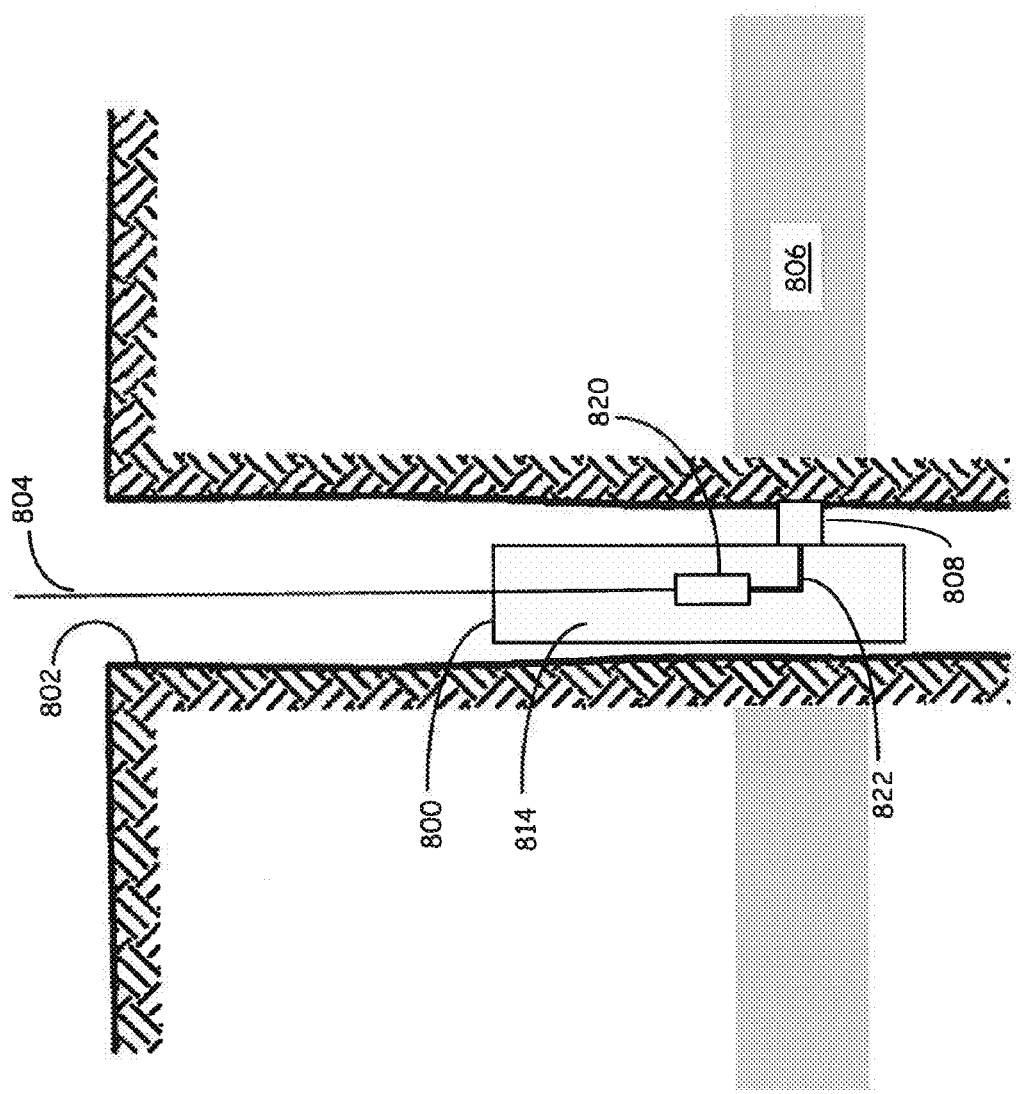
FIG. 19 shows a schematic diagram wellbore deployment of a tool including a sample chamber having a patterned structure.

In some embodiments, the chamber can be integrated into a downhole fluid analysis module, such as an optical analyzer adapted to receive at least a portion of the fluid sample. An example of a downhole tool is illustrated in FIG. 19. The tool 800 is being deployed within a wellbore 802. The tool 800 can be deployed, for example, from a wire line truck (not shown).

A wireline cable 804 is deployed into the well 802. The downhole sampling tool 800 is disposed at the end of the cable 804, shown lowered in a vicinity of a subterranean formation 806. According to some embodiments, the downhole sampling tool 800 performs focused fluid extraction using a flowline extraction probe 808. For example, a formation fluid extraction tool 808, such as the focused fluid extraction tool known as a Quicksilver Probe, available in the commercial services provided by Schlumberger Technology Corporation, Sugar Land, Tex., USA. The Quicksilver Probe flowline extraction probe 808 is part of the Modular Formation Dynamics Tester (MDT) tool suite, also available in the commercial services provided by Schlumberger.

In some embodiments, the tool 800 also includes a downhole fluid analysis module 814, such as an optical analyzer adapted to receive at least a portion of the fluid sample. The optical analyzer 814 can be configured to determine an optical property of the fluid sample and to provide an output signal related to or otherwise indicative of the optical property. An example of such an optical analyzer is the Composition Fluid Analyzer (CFA) module of the MDT tool suite. The CFA module 814 is configured to perform near-infrared optical absorption spectrometry and fluorescence emission measurements for analyzing fluids as they flow through the tool 800. In at least some embodiments, the fluid analysis module 814 includes a sample chamber 820. A fluid sample (e.g., a gaseous sample) is routed to the sample chamber 820 via a flowline 822. Any of the gaseous sample chambers described herein can represent sample chambers of existing tools, such as the CFA module 814, the module having been modified as described herein. Alternatively the chamber can be in a dedicated tool for performing thermodynamic evaluation of a fluid sample according to the techniques described herein. Another example of an optical analyzer is the live fluid analyzer (LFA), also part of the Modular Formation Dynamics Tester (MDT) tool suite, available in the commercial services provided by Schlumberger Technology Corporation, Sugar Land, Tex., USA. The LFA supports downhole fluid identification using optical techniques to analyze fluids as they flow through the tool. The LFA module employs an absorption spectrometer that utilizes visible and near-infrared light to quantify the amount of reservoir and drilling fluids that are in the flow line. Light is transmitted through the fluid and measured as it flows past the LFA spectrometer. The amount of light absorbed by the fluid depends on the composition of the fluid. Water and oil are reliably detected by their unique absorption spectra. In at least some embodiments, a fluid sample analyzer can include more than one sensor for differentiating between gas and liquid. For example, multiple optical sensors can be provided to measure absorption of light at two spectra, such as 1671 nm (methane spectrum) and 1725 nm ("dead" oil spectrum).

It is understood that downhole applications, such as those referred to herein, can include any downhole activities related to the extraction of oil and natural gas. As such, applications can include testing during various phases of drilling, such as drill stem testing, completion and production. It is also understood that the devices and techniques described herein are by no way limited to downhole applications. For example, such devices and techniques can be applied during surface testing also related to the extraction of oil and natural gas. Such surface activities can be accomplished at a well site or at another location, such as a laboratory. It is further understood that although the embodiments describe herein relate to the extraction of oil and natural gas, the devices and techniques have broader applications, such as in detecting dew dropout during pipeline transportation of gaseous fluids, such as natural gas.

The embodiments discussed herein are directed to dew that drops out from a retrograde condensate, but it is understood that the technology here could apply to dew produced from other thermodynamic systems as well.

The term "live fluid" such as live oil is commonly used to refer to pressurized reservoir fluid samples that remain in single phase. Additionally, for the purpose of clarity, the term "analyte" is herein used to refer to a fluid sample that is undergoing analysis. In accordance with the present invention, the analyte may be single phase or multiphase and may include a liquid hydrocarbon phase, a water phase, or a gaseous hydrocarbon phase.

Whereas many alterations and modifications of the present invention will no doubt become apparent to a person of ordinary skill in the art after having read the foregoing description, it is to be understood that the particular embodiments shown and described by way of illustration are in no way intended to be considered limiting. Further, the invention has been described with reference to particular preferred embodiments, but variations within the spirit and scope of the invention will occur to those skilled in the art. It is noted that the foregoing examples have been provided merely for the purpose of explanation and are in no way to be construed as limiting of the present invention.

While the present invention has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present invention in its aspects.

Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

We claim:

1. A condensate detector, comprising:
   a gaseous sampling chamber defining an interior volume;
   a patterned structure forming a roughened surface at least partially exposed to the interior surface of the gaseous sampling chamber, the patterned structure comprising an open volume accessible by the roughened surface, the open volume being at least about 10% of the interior volume of the gaseous sampling chamber;
   an illumination source configured to illuminate at least a portion of the patterned structure;
   a light detector configured to receive at least a portion of illumination returned from the patterned structure; and
   a condensate detector in communication with at least the light detector, and configured to determine a presence of a condensate on the roughened surface in response to returned illumination received at the light detector.

2. The condensate detector of claim 1, wherein the light detector comprises a detector array configured to selectively detect illumination returned from the patterned structure.

3. The condensate detector of claim 2, wherein the detector array is configured to detect illumination according to wavelength.

4. The condensate detector of claim 2, wherein the detector array is configured to detect illumination that is offset from a reflected ray.

5. The condensate detector of claim 1, wherein the roughened surface of the patterned structure comprises a plurality of surface features.

6. The condensate detector of claim 5, wherein the plurality of surface features comprises at least one of holes and rods.

7. The condensate detector of claim 5, wherein the surface features of the plurality of surface features are arranged periodically.

8. The condensate detector of claim 5, wherein the surface features of the plurality of surface features are arranged randomly.

9. The condensate detector of claim 1, further comprising a second illumination source configured to optically excite condensate on the patterned structure sufficiently to induce fluorescence in the condensate, when present, and a light detector configured to detect fluorescent spectra, the presence of condensate determinable from the detected fluorescent spectra.

10. The condensate detector of claim 1, further comprising at least one window aligned between the roughened surface and each of the illumination source and the light detector, the at least one window isolating the illumination source and light detector from exposure to gaseous samples within the chamber, while allowing for efficient transmission of the illumination and the returned illumination therethrough.

11. The condensate detector of claim 10, wherein the window comprises the patterned structure.

12. The condensate detector of claim 1, further comprising a thermal source in thermal communication with the patterned structure, the thermal source operable to change a temperature of the roughened surface.

13. The condensate detector of claim 1, wherein the gaseous chamber is sealable and reconfigurable to at least one of increase and decrease the interior volume, inducing a corresponding change in pressure of a sample gas contained therein.

14. The condensate detector of claim 1, further comprising an outer layer disposed at least upon the roughened surface exposed to the gaseous sampling chamber, the outer layer operable to preferentially condense one of a water and a hydrocarbon.

15. The detector of claim 1, wherein the condensate detector is configured to determine a quantity of a condensate on the roughened surface in response to returned illumination received at the light detector.

16. A method for detecting a condensate in a gaseous sample, the method comprising:
receiving the gaseous sample within a chamber defining an enclosed interior volume;
exposing a patterned structure forming a roughened surface to the gaseous sample, the patterned structure comprising an open volume accessible by the roughened surface, the open volume being at least about 10% of the interior volume of the chamber;
illuminating the patterned structure;
detecting at least a portion of the illumination returned from the patterned structure; and
determining from the detected illumination a presence of the condensate on the roughened surface.

17. The method of claim 16, wherein illuminating the patterned structure comprises optically exciting condensate on the patterned structure sufficiently to induce fluorescence in a condensate, when present, the act of detecting the illumination comprising detecting fluorescent spectra, the presence of condensate determinable from the detected fluorescent spectra.

18. The method of claim 17, further comprising determining from the detected illumination, a relative volume fraction dropout.

19. The method of claim 16, wherein the act of detecting at least a portion of the illumination comprises detecting reflected illumination, the presence of condensate on the roughened surface determinable from the reflected illumination.

20. The method of claim 16, wherein the act of detecting at least a portion of the illumination comprises detecting scattered illumination, the presence of condensate on the roughened surface determinable from the scattered illumination.

21. The method of claim 14, wherein scattered illumination is detected offset from the reflected ray.

22. The method of claim 16, further comprising varying at least one of a temperature and a pressure of the gaseous sample and repeating the acts of exposing, illuminating, detecting and determining a presence of the condensate.

23. The method of claim 22, wherein the act of varying at least one of a temperature and a pressure comprises reducing a pressure, the pressure at which a presence of the condensate on the roughened surface is determined being indicative of a retrograde dew point.

24. The method of claim 16, further comprising selectively evaporating the condensate from the roughened surface.

25. The method of claim 16, further comprising selectively rejecting one of water and an oil from the opened surface of the roughened surface.

26. The method of claim 16, wherein at least the act of determining a presence of the condensate is accomplished under the control of a processor executing a set of pre-programmed instructions.

27. An apparatus, comprising:
means for exposing a patterned structure forming a roughened surface to a gaseous sample, the means for exposing comprising an interior volume and the patterned structure comprising an open volume accessible by the roughened surface, the open volume being at least about 10% of the interior volume;
means for illuminating the patterned structure;
means for detecting at least a portion of the illumination returned from the patterned structure; and
means for determining from the detected illumination a presence of the condensate, at least one of reflectivity or scattering cross section of the patterned surface being indicative of condensate on the on the roughened surface.

* * * * *